(12) United States Patent
Moutet et al.

(10) Patent No.: US 9,452,126 B2
(45) Date of Patent: Sep. 27, 2016

(54) PHARMACEUTICAL/COSMETIC COMPOSITIONS COMPRISING HYALURONIC ACID AND TREATMENT OF DERMATOLOGICAL CONDITIONS THEREWITH

(71) Applicant: Galderma Research & Development, Biot (FR)

(72) Inventors: Marc Moutet, Cachan (FR); Jean-Claude Yadan, Montreuil sous Bois (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 14/106,064

(22) Filed: Dec. 13, 2013

(65) Prior Publication Data
US 2014/0142062 A1    May 22, 2014

Related U.S. Application Data

(63) Continuation of application No. 13/360,588, filed on Jan. 27, 2012, now abandoned, which is a continuation of application No. 12/213,690, filed on Jun. 23, 2008, now abandoned, which is a continuation of application No. PCT/FR2006/051391, filed on Dec. 19, 2006.

(30) Foreign Application Priority Data

Dec. 21, 2005 (FR) ..................... 05 13055

(51) Int. Cl.
| | |
|---|---|
| A61K 8/34 | (2006.01) |
| A61K 8/60 | (2006.01) |
| A61K 8/73 | (2006.01) |
| A61K 8/63 | (2006.01) |
| A61K 8/67 | (2006.01) |
| A61K 9/00 | (2006.01) |
| A61K 31/07 | (2006.01) |
| A61K 31/702 | (2006.01) |
| A61K 31/704 | (2006.01) |
| A61K 31/728 | (2006.01) |
| A61K 47/12 | (2006.01) |
| A61K 47/26 | (2006.01) |
| A61Q 19/00 | (2006.01) |
| A61Q 19/08 | (2006.01) |
| A61K 47/10 | (2006.01) |
| A61K 47/28 | (2006.01) |

(52) U.S. Cl.
CPC ............ *A61K 8/735* (2013.01); *A61K 8/342* (2013.01); *A61K 8/60* (2013.01); *A61K 8/63* (2013.01); *A61K 8/671* (2013.01); *A61K 9/0014* (2013.01); *A61K 9/0019* (2013.01); *A61K 31/07* (2013.01); *A61K 31/702* (2013.01); *A61K 31/704* (2013.01); *A61K 31/728* (2013.01); *A61K 47/10* (2013.01); *A61K 47/12* (2013.01); *A61K 47/26* (2013.01); *A61K 47/28* (2013.01); *A61Q 19/00* (2013.01); *A61Q 19/08* (2013.01)

(58) Field of Classification Search
CPC .......... A61K 8/63; A61K 8/60; A61K 8/342; A61K 8/735; A61K 8/671; A61K 8/0014; A61K 8/0019; A61K 31/704; A61K 31/728; A61K 47/12; A61K 47/26; A61K 47/28; A61K 47/10; A61K 2300/00; A61Q 19/00; A61Q 19/08
USPC ........................................... 514/54
See application file for complete search history.

(56) References Cited

U.S. PATENT DOCUMENTS

| | | | | |
|---|---|---|---|---|
| 5,723,139 | A | * | 3/1998 | Granger et al. ............. 424/401 |
| 5,739,113 | A | * | 4/1998 | Lee ............................. 424/488 |
| 5,849,324 | A | * | 12/1998 | Dohnalek et al. ........... 424/440 |
| 6,024,941 | A |   | 2/2000 | Yanagida et al. |
| 6,099,844 | A | * | 8/2000 | Rohde et al. ............... 424/728 |

FOREIGN PATENT DOCUMENTS

| | | | | |
|---|---|---|---|---|
| EP | 0 608 433 B1 | | 5/2004 | |
| EP | 0608433 | * | 5/2004 | ............ A61K 7/00 |
| WO | 03/008457 | * | 1/2003 | ............ C08B 37/00 |
| WO | 03/008547 A2 | | 1/2003 | |
| WO | 2005/039532 | | 5/2005 | |
| WO | WO 2005/039532 A1 | * | 5/2005 | ............ A61K 9/10 |

OTHER PUBLICATIONS

Lautenschlager, Hans., "Hyaluronic acid—a legendary agent", Kosmetische Praxis, 2008, vol. 4, pp. 16-18.

* cited by examiner

*Primary Examiner* — Ganapathy Krishnan
(74) *Attorney, Agent, or Firm* — Dentons US LLP

(57) ABSTRACT

Pharmaceutical/cosmetic compositions containing a dermatologically effective amount of hyaluronic acid, at least one retinoid and/or salt and/or derivative thereof, at least one oligosaccharide and at least one inhibitor of hyaluronic acid degradation, formulated into a physiologically acceptable medium therefor, are useful for the treatment of wrinkles, fine lines, fibroblast depletions and scars.

20 Claims, 1 Drawing Sheet

PHARMACEUTICAL/COSMETIC COMPOSITIONS COMPRISING HYALURONIC ACID AND TREATMENT OF DERMATOLOGICAL CONDITIONS THEREWITH

CROSS-REFERENCE TO EARLIER APPLICATIONS

This application is a continuation of U.S. patent application Ser. No. 13/360,588, filed Jan. 27, 2012, which is a continuation of U.S. patent application Ser. No. 12/213,690, filed Jun. 23, 2008, which is a continuation of PCT/FR 2006/051391, filed Dec. 19, 2006 and designating the United States (published in the French language on Jul. 5, 2007 as WO 2007/074288 A1; the title and abstract were also published in English), which claims priority under 35 U.S.C. §119 of FR 0513055, filed Dec. 21, 2005, each hereby expressly incorporated by reference in its entirety and each assigned to the assignee hereof.

BACKGROUND OF THE INVENTION

1. Technical Field of the Invention

The present invention relates to preparations for topical and/or parenteral administration, comprising hyaluronic acid formulated into a physiologically acceptable medium, to processes for the production of such preparations, and to uses thereof as a medicament, such preparations being especially useful for the treatment of dermatological conditions and afflictions, in particular for the treatment of wrinkles, fine lines, fibroblast depletions and any scars.

2. Description of Background and/or Related and/or Prior Art

Skin aging is one of the most visible modifications of the process of senescence. In addition, the skin is exposed to many factors that accelerate this physiological process. A distinction can be made from two different types of skin aging. Firstly, intrinsic aging, that it is easier to evaluate on areas which are not normally exposed to the sun and, secondly, extrinsic aging, brought about by the interaction of environmental factors, in particular UV rays. These environmental factors have a much more marked effect on the parts of the body exposed to the sun, especially in individuals of light phototype. This is then also referred to as actinic aging. Other factors, such as dietary habits, smoking, excessive alcohol consumption, chronic diseases and endocrine gland dysfunctions, also contribute to this aging.

During intrinsic skin aging, the horny layer is relatively unmodified. The epidermis is atrophic and the dermal-epidermal junction is flattened, such that the adhesion to the dermis is weaker, facilitating the formation of bubbles. The thickness of the dermis is clearly reduced; there are fewer blood vessels. Fewer fibroblasts are also observed and their biosynthetic and proliferative capacities are reduced. The elastic fibers first undergo modifications, and subsequently disappear.

As regards extrinsic aging, an irregular, sometimes atrophic, sometimes hyperplasic, epidermis is observed, with signs of disorganization and of dysplasia. There are more melanocytes in certain areas, and fewer in others. The distribution of melanin in the epidermis is also irregular, subsequent to melanosome transfer problems. The number of Langerhans cells decreases. The small blood vessels are first dilated, and then become thinner and atrophy.

Wrinkles are the most visible signs of aging. A distinction can be made from several types, in particular superficial and deep wrinkles. Deep wrinkles are thought to be due to dermo-hypodermal modifications, whereas superficial wrinkles could be explained by dermal and possibly epidermal modifications. Wrinkles are especially due to the loss of elasticity of the skin. The effect on the subepidermal elastic network gives rise to superficial laxity of the aged skin and folding of its surface. The destruction of the elastic fibers in the reticular dermis is responsible for the loss of elasticity and of the skin's ability to return to its shape after stretching. A suitable treatment will be possible according to the type, the intensity and the topography.

The treatment of unattractive skin modifications related to aging has made enormous progress over the past few years.

A relatively large number of natural or synthetic substances have already been described as dermal implants, i.e., as substances injected directly into the skin, in order to remedy skin alterations resulting from aging, traumas or diseases.

Other therapeutic alternatives for these applications are in particular the local injection of botulinum toxin (Botox®) or the use of laser techniques. These various types of treatment are not exclusive and a combination thereof has even been recommended. Among the natural substances of human origin, collagen and hyaluronic acid are those which form the basis of the majority of products available on the market.

Hyaluronic acid is a ubiquitous natural polysaccharide which exists in the same form from the simplest bacterium to humans. It is a polymer of disaccharides which are themselves composed of D-glucuronic acid and N-acetylglucosamine, linked to one another by alternating beta-1,4 and beta-1,3 glycosidic linkages. The polymers of this recurring unit may be from 102 and 104 kDa in size, in vivo. Hyaluronic acid represents in particular a natural constituent of the dermis, where it plays an important role in the hydration and elasticity of the skin. However, it decreases in amount and in quality with age, leading to drying out of the skin, which becomes wrinkled. It is highly water-soluble and forms high-viscosity solutions in water. Because of these specific properties, hyaluronic acid is among the pharmaceutical products most commonly used.

However, in humans, hyaluronic acid is very rapidly eliminated from the plasma by degradation. Its plasma half-life after intravenous injection is very short, from 2.5 to 0.5 minutes, whereas in the skin, its half-life is from 0.5 to 2 days depending on its concentration. Its excretion in the urine is low, less than 1% of total clearance. In rabbits, the rate of elimination, in the skin, has been measured (Reed R K, Laurent U B, Fraser J R, Laurent T C. Removal rate of [3H]hyaluronan injected subcutaneously in rabbits, *Am. J. Physiol.*, 1990 August; 259 (2 Pt 2): H532-5). It is non-exponential with a half-life of 0.5 to 1 day when its concentration is 5 mg/ml.

The tolerance of hyaluronic acid is very good and no immunogenicity has been associated with this substance. A very low incidence of side effects is thus observed.

The use of hyaluronic acid, alone or in combination, has thus been described for several medical applications, such as, for example, the treatment of osteoarthritis and also rheumatoid arthritis. Injectable compositions such as, for example, hyaluronic acid alone, collagen alone or the combination of "hyaluronic acid and collagen" have also already been employed in repair surgery, in the context of the treatment by filling of wrinkles, fine lines, fibroblast depletions and any scars.

Currently, many dermal implants are used but none has yet been considered to be ideal in the context of a safe and healthy tissue augmentation (Naoum C, Dasiou-Plakida D.

Dermal filler materials and botulin toxin, *Int. J. Dermatol.,* 2001 October; 40(10): 609-21).

However, because the bioavailability of hyaluronic acid is too low after injection and its injection frequency is too high, it cannot be used as such.

Of course, there has been an effort to develop compositions based on hyaluronic acid having a very good bioavailability and capable of more successfully withstanding the action of degradation enzymes. This makes it possible, in particular, to space out the procedures and to reduce the number thereof.

These compositions employed as a dermal implant are all composed of stabilized hyaluronic acid and a large number of these comprise hyaluronic acid that has been chemically modified for this purpose. In addition, the hyaluronic acid included in these products is predominantly of nonhuman origin, for instance of avian or bacterial origin.

Numerous chemically modified hyaluronic acid derivatives in the form, in particular, of esters, amides and also derivatives having "intra- and/or interchain bridges" (crosslinked), are thus found in these compositions.

However, these modifications affect the physicochemical characteristics and the biological properties of hyaluronic acid, and also its outcome after administration. These structural modifications of hyaluronic acid can lead to inflammatory reactions, as reported by Sopaar C N S, Patrinely J R Ophthalmic plastic and reconstructive surgery 2005 March; 21(2): 151-53.

Furthermore, the bioavailability of these hyaluronic acid derivatives, although better than that of natural hyaluronic acid, still remains too short.

SUMMARY OF THE INVENTION

Novel preparations comprising hyaluronic acid have now been developed having a better bioavailability while at the same time conserving the physicochemical characteristics and biological properties thereof, as well as a process for the formulation of such preparations.

Thus, the present invention features pharmaceutical or cosmetic compositions or preparations, in particular for topical and/or parenteral administration, comprising, formulated into a physiologically acceptable medium, hyaluronic acid, and also:
  at least one retinoid and/or salts thereof and/or derivatives thereof,
  at least one oligosaccharide, and
  at least one inhibitor of hyaluronic acid degradation.

The present invention also features a process for the production of a pharmaceutical or cosmetic composition or preparation for topical and/or parenteral application, comprising, in a physiologically acceptable medium, hyaluronic acid, and at least one retinoid and/or salts thereof and/or derivatives thereof, at least one oligosaccharide and at least one inhibitor of hyaluronic acid degradation, which comprises the step of mixing an effective amount of hyaluronic acid with at least one retinoid and/or salts thereof and/or derivatives thereof, at least one oligosaccharide and at least one inhibitor of hyaluronic acid degradation. Preferably, the process according to the invention also comprises a step of preparing a physiologically acceptable medium, in which the active agents are mixed.

Finally, this invention features administration of the subject preparations as medicaments for the treatment and/or prevention of dermatological conditions/afflictions, whether comprising a regime or regimen.

When a pharmaceutical or cosmetic composition or preparation for topical and/or parenteral application comprises, formulated into a physiologically acceptable medium, hyaluronic acid, and at least one retinoid and/or salts thereof and/or derivatives thereof, at least one oligosaccharide and at least one inhibitor of hyaluronic acid degradation, it clearly increases the bioavailability of the hyaluronic acid, it makes it possible to space out the applications and to reduce the number thereof and it is highly effective in filling wrinkles, fine lines, fibroblast depletions and any scars.

BRIEF DESCRIPTION OF THE DRAWINGS

The invention will be understood more clearly from the description to follow and the attached Figures of Drawing, in which.

Figure 1:
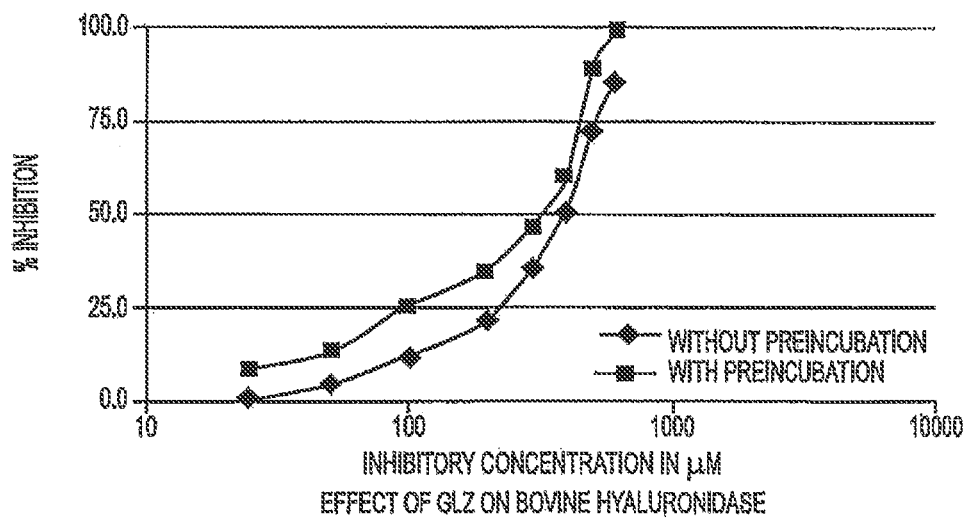
FIG. 1 shows, in a semilogarithmic representation, the results of a study, the objective of which was to evaluate the inhibitory effect of glycyrrhizin on hyaluronidase activity of bovine origin.

DETAILED DESCRIPTION OF BEST MODE AND SPECIFIC/PREFERRED EMBODIMENTS OF THE INVENTION

The preparations according to the invention comprise, formulated into a physiologically acceptable medium, hyaluronic acid, and at least one retinoid and/or salts thereof and/or derivatives thereof, at least one oligosaccharide and at least one inhibitor of hyaluronic acid degradation.

The present invention thus also features products comprising:
  hyaluronic acid,
  at least one retinoid and/or salts thereof and/or derivatives thereof,
  at least one oligosaccharide, preferably one, and
  at least one inhibitor of hyaluronic acid degradation, preferably one, as a combination product for simultaneous, separate or sequential administration in the treatment of dermatological conditions.

Such a combination product is in particular effective in the treatment of wrinkles, fine lines, fibroblast depletions and scars.

The term "combination product" means a single composition comprising each of the active compounds, but also a complex composition comprising at least two different compositions, each comprising a part of the active agents of said preparation.

The term "active agents" means, according to the present invention, the compounds selected from hyaluronic acid, at least one oligosaccharide, at least one inhibitor of hyaluronic acid degradation and at least one retinoid and/or salts thereof and/or derivatives thereof. Thus, the combination product according to the invention comprises at least 4 active agents.

Exemplary combination products according to the invention include:
  a single composition comprising hyaluronic acid, a retinoid and/or salts thereof and/or derivatives thereof, an oligosaccharide and an inhibitor of hyaluronic acid degradation;

a composition comprising just one of these four active agents, combined with a composition comprising at least the other three active agents;

a composition comprising two of these four active agents, combined with a composition comprising at least the other two active agents; and a composition comprising three of these four active agents, combined with a composition comprising at least the fourth active agent.

Preferably, the combination product according to the invention comprises a composition A comprising hyaluronic acid in the form of an injectable (preferably aqueous) solution, combined with a composition B comprising:

at least one inhibitor of hyaluronic acid degradation, preferably glycyrrhizin, at least one oligosaccharide, preferably the pentamer (NAG-glucuronic acid)5, and at least one retinoid and/or salts thereof and/or derivatives thereof, preferably retinal, in the form of a composition for topical application.

The term "physiologically acceptable medium" means, according to the invention, a medium compatible with the skin and, optionally, with its appendages (eyelashes, nails, hair) and/or the mucous membranes.

In the preparations according to the invention, the hyaluronic acid, the retinoid and/or salts thereof and/or derivatives thereof, the oligosaccharide and the inhibitor of hyaluronic acid degradation are present in proportions that can range from 0.0000001% to 10%, preferably from 0.00001% to 1% by weight, relative to the total weight of the preparation. In the present description, and unless otherwise specified, it is understood that, when concentration ranges are given, they include the upper and lower limits of said range.

The preparations according to the invention comprise hyaluronic acid.

The term "hyaluronic acid" means the compound constituted of the series of glucuronic acid and of N-acetylglucosamine.

Advantageously, the hyaluronic acid is natural.

The term "natural hyaluronic acid" means a hyaluronic acid that is non-stabilized and non-chemically modified in the form, in particular, of esters or amides or in the form of derivatives having "intra- and/or interchain bridges" (cross-linked), such modifications affecting the physicochemical characteristics and the biological properties of said hyaluronic acid, and also what becomes of it after administration.

The preparations according to the invention also comprise a retinoid and/or salts thereof and/or derivatives thereof, taken alone or as a mixture.

Among the retinoids that may be part of the preparations according to the invention, retinol, retinal and/or retinoic acid, and salts and derivatives thereof, taken alone or as a mixture, will preferably be selected, more preferably retinol.

The term "retinoid salt" means, in particular, an alkali metal salt, an alkaline-earth metal salt or an organic amine salt. The term "retinoid derivative" means in particular the esters, such as retinyl palmitate, retinyl acetate, retinyl stearate, retinyl oleate, retinyl propionate or else retinyl linoleate.

Advantageously, the retinoids included in the preparations according to the invention are retinoids that exist naturally in the human body.

The preparations according to the invention also comprise an oligosaccharide.

The term "oligosaccharide" means, in particular, any oligosaccharide which limits the penetration of hyaluronic acid into the cells of the skin, in particular the keratinocytes and the fibroblasts.

Among the oligosaccharides, taken alone or as a mixture, that may be part of the preparations according to the invention, hyaluronic acid oligomers, preferably hyaluronic acid trimers to decamers, more preferably hyaluronic acid tetramers to hexamers, more preferentially the hyaluronic acid pentamer, will be selected.

Advantageously, the oligosaccharides used in the preparations according to the invention are compounds that exist naturally in the human body.

In the preparations according to the invention, the oligosaccharide is used at concentrations of from $10^{-9}$ M and $10^{-3}$ M, preferably from $10^{-8}$ M and $10^{-5}$ M.

The preparations according to the invention also comprise an inhibitor of hyaluronic acid degradation.

The term "inhibitor of hyaluronic acid degradation" means a compound capable of reducing, or even blocking, either the extracellular or the intracellular catabolism of hyaluronic acid, preferably a compound capable of reducing, or even blocking, the extracellular catabolism of hyaluronic acid, more preferably a compound capable of inhibiting the extracellular hyaluronidase present in the skin.

Among the inhibitors of hyaluronic acid degradation, taken alone or as a mixture, that may be included in the preparations according to the invention, glycyrrhizin or glycyrrhetinic acid, and derivatives and/or analogs thereof, will in particular be selected.

Advantageously, the inhibitors of hyaluronic acid degradation included in the preparations according to the invention are natural.

In the preparations according to the invention, the inhibitor is present at concentrations of from $10^{-9}$ M and $10^{-2}$ M, preferably from $10^{-6}$ M and $10^{-3}$ M.

The term "derivatives of glycyrrhizin or of glycyrrhetinic acid" means, in particular, the salts, the substituted derivatives, the enantiomers and the racemates of said compounds.

As salts of said compounds, exemplary are the salts obtained by addition of said compounds with an inorganic base, selected in particular from among sodium hydroxide, lithium hydroxide, calcium hydroxide, potassium hydroxide, magnesium hydroxide, ammonium hydroxide or zinc hydroxide, and alkali metal or alkaline-earth metal carbonates such as sodium, lithium, calcium, potassium, magnesium, ammonium or zinc carbonates and bicarbonates, or with an organic base, selected, in particular, from among methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, procaine, lysine, arginine, histidine, N-methylglucamine or else phosphonium salts such as alkylphosphonium salts, arylphosphonium salts, alkylarylphosphonium salts, alkenylarylphosphoniums or quaternary ammonium salts such as tetra-n-butylammonium salts. Such salts are in particular the potassium salt of glycyrrhetinic acid, the sodium salt of glycyrrhetinic acid, or else the monoammonium salt of glycyrrhetinic acid (ammonium glycyrrhetinate).

The term "analog" means, in particular, the enzymatic or biomimetic analogs of said compounds, capable of binding to the catalytic or noncatalytic site of hyaluronidases and of thus inhibiting their activation. Such analogs may be selected, in vitro, by means of hyaluronidase binding or inhibition assays according to the techniques conventionally used.

Advantageously, the derivatives and/or analogs should be of natural origin.

The compounds and derivatives and/or analogs thereof of natural origin are compounds in the pure state or in solution at various concentrations, obtained by various methods for extracting or hydrolyzing biological material of natural origin.

In a known manner, the preparations according to the invention may also contain the usual adjuvants known to those skilled in the art.

The preparations according to the invention are formulated for topical and/or parenteral application.

When they are for topical application, the preparations may be in any of the galenical forms normally employed for topical administration. Exemplary topical preparations include preparations in liquid, pasty or solid form, and more particularly in the form of ointments, aqueous, aqueous-alcoholic or oily solutions, dispersions of the optionally two-phase lotion type, serum, aqueous, anhydrous or lipophilic gels, powders, impregnated pads, syndets, wipes, sprays, foams, sticks, shampoos, compresses, washing bases, emulsions of liquid or semi-liquid consistency of the milk type, obtained by dispersion of a fatty phase in an aqueous phase (O/W) or vice versa (W/O), a microemulsion, suspensions or emulsions of soft, semi-liquid or solid consistency of the white or colored cream, gel or ointment type, suspensions of microspheres or nanospheres or lipid or polymeric vesicles, or microcapsules, microparticles or nanoparticles or polymeric or gelled patches for controlled release.

When they are for parenteral administration, the preparations according to the invention may be administered subcutaneously or intradermally. Exemplary parenteral preparations include preparations in the form of solutions or suspensions for perfusion or for injection.

According to the invention, the compounds constituting the preparation may be administered according to the same method of administration or according to a combined method of administration.

The term "combined method of administration" means the administration of one or more compound(s) of the preparation according to the invention by topical administration combined with a parenteral administration, in particular by subcutaneous or intradermal injection of the other compound(s) of the preparation.

Advantageously, one fraction of the compounds is first applied topically and another fraction of said compounds is then applied parenterally, or vice versa.

According to an alternative embodiment of the invention, it is also possible to simultaneously apply one fraction of the compounds topically and another fraction of said compounds parenterally.

Indeed, the hyaluronic acid may even be administered in the form of an injectable aqueous solution, the retinol, the hyaluronic acid pentamer and the glycyrrhizin being administered in the form of a cream.

In the context of a combined administration, the administration frequencies may be identical or different.

As one example, the frequency of administration of hyaluronic acid injected in the form of an injectable aqueous solution may range from 1 to 12 months, preferably from 6 to 12 months, whereas those of the other compounds of the preparation according to the invention, administered in the form of a cream, may range from 1 to 7 days, preferably from 1 to 3 days.

The process for the production a preparation according to the invention comprises a step of mixing an effective amount of hyaluronic acid, at least one retinoid and/or salts thereof and/or derivatives thereof, at least one oligosaccharide and at least one inhibitor of hyaluronic acid degradation. Preferably, said process comprises a step of preparing a physiologically acceptable medium, to which the active agents are added.

According to a specific embodiment of the invention, the process for the production of a preparation comprises the steps of preparing a physiologically acceptable medium and of mixing an effective amount of hyaluronic acid, retinol, hyaluronic acid pentamer, and glycyrrhizin and/or derivatives thereof and/or analogs thereof.

Advantageously, the process for the production of a combination product according to the invention comprises a first step of preparing an injectable solution, comprising mixing the hyaluronic acid with a physiologically acceptable medium, and a second step of preparing a formulation suitable for topical administration, comprising mixing at least one retinoid and/or salts thereof and/or derivatives thereof, with at least one oligosaccharide and at least one inhibitor of hyaluronic acid degradation in a physiologically acceptable medium.

The present invention also features administration of a preparation as described above as a medicament useful in the treatment and/or prevention of dermatological conditions/afflictions.

More particularly, this invention features administration of a preparation as described above as a medicament useful in the treatment of wrinkles, fine lines, fibroblast depletions and scars. Such a medicament is suitable for the treatment of wrinkled and/or aged skin, and is useful, in particular, to prevent and/or reduce the effects thereof. The treatment of wrinkles, fine lines, fibroblast depletions and any scars is carried out in particular by filling.

In particular, the preparations according to the invention may be applied to the areas of the face or of the forehead that are marked with expression wrinkles.

The present invention also features administration of a preparation as described above as a medicament useful in repair surgery.

In addition, this invention features such preparations within a dermal implant.

In order to further illustrate the present invention and the advantages thereof, the following specific examples are given, it being understood that same are intended only as illustrative and in nowise limitative. In said examples to follow, all parts and percentages are given by weight, unless otherwise indicated.

Example 1

Inhibitory Effect of Glycyrrhizin (GLZ) on Hyaluronidase Activity of Bovine Origin Determination of the $IC_{50}$ of GLZ, with or without Pre-Incubation at 37° C.:

GLZ, at various concentrations, is or is not pre-incubated for 20 minutes at 37° C. in the presence of the enzyme. The enzyme reaction is triggered by adding the hyaluronic acid solution (time T0). After incubation for 20 minutes, the non-hydrolyzed hyaluronic acid is precipitated by adding acidic bovine albumin solution.

In order to verify that the pre-incubation step has no effect on the stability of the hyaluronidase, an aliquot of a solution of the enzyme is placed at 37° C. for 20 minutes. Another aliquot is conserved in an ice bath for 19 minutes, and is then incubated at 37° C. for 1 minute. A solution of hyaluronic acid is then added to each aliquot (T0). After incubation for 15, or 45 minutes, the non-hydrolyzed hyaluronic acid is precipitated by addition of acidic bovine albumin solution.

Measurement of the Hyaluronidase Activity of Bovine Origin:

After the precipitation step, the turbidimetry of the solutions is determined on a spectrophotometer at a wavelength of 600 nm. The optical density (OD) of these solutions is subtracted from the OD of a control solution of hyaluronic acid (of the same concentration) not hydrolyzed by the enzyme. This difference in OD, which is inversely proportional to the concentration of hyaluronic acid, is used to measure the activity of the hyaluronidase.

The inhibitory effect of GLZ on the bovine hyaluronidase is shown in FIG. 1 (semilogarithmic representation).

The results obtained show that this effect is dose-dependent and that the concentration of GLZ which gives 50% inhibition (1050) of the hyaluronidase activity is 400 µM without pre-incubation with the enzyme.

When the GLZ is pre-incubated for 20 minutes at 37° C. in the presence of the enzyme, the $IC_{50}$ is 350 µM.

Example 2

Inhibitory Effect of the "GLZ+Pentamer (NAG-Glucuronic Acid)5+Retinol" Combination on the Neosynthesis of Hyaluronic Acid by Normal Human Keratinocytes According to the prior art, it is accepted that an equilibrium pre-exists from the neosynthesis and the degradation of hyaluronic acid. In other words, the neosynthesis of hyaluronic acid is a reflection of its degradation; measuring the variations in one therefore amounts to measuring the variations in the other. For reasons of technical simplicity, the change in neosynthesis of hyaluronic acid in the presence of the "GLZ+pentamer (NAG-glucuronic acid)5+retinol" combination is measured, relative to the corresponding control.

The adult human keratinocytes (NHK) are isolated from a fragment of human skin collected after an abdominoplasty operation (subject CAOL, 38 years old).

The NHK are cultured to confluence as a monolayer in 24-well plates and sub-cultured. The NHK are used following the third passage.

The culture medium used is MCK medium at 37° C. in a humid atmosphere containing 5% $CO_2$.

The MCK culture medium is an SFM defined keratinocyte medium comprising growth factors, to which penicillin (50 IU/ml) and streptomycin (50 µg/ml) are added.

Preparation of Reagents:

The pentamer (NAG-glucuronic acid)5 is dissolved at 2 mg/ml in the MIK culture medium (MCK medium containing 2 µCi/ml of radiolabeled glucosamine). It is then diluted in an MIK medium containing 0.2% DMSO.

This product is tested at 0.1-0.5 and 2 mg/ml.

The glycyrrhizin (GLZ) is dissolved at 400 mM in DMSO. It is then diluted in the MIK culture medium (MCK medium containing 2 µCi/ml of radiolabeled glucosamine).

This product is tested at 100-400 and 800 µM (concentration of DMSO kept constant: 0.2%).

The retinal is dissolved at 10 mM in DMSO. It is then diluted in the MIK culture medium (MCK medium containing 2 µCi/ml of radiolabeled glucosamine).

This product is tested at 1-10 and 100 nM (concentration of DMSO maintained constant: 0.2%).

The "GLZ+pentamer (NAG-glucuronic acid)5+retinal" combination is prepared by mixing the stock solutions prepared above. It is then diluted in MIK medium (MCK medium containing 2 µCi/ml of radiolabeled glucosamine).

This product is tested at:

100 µM GLZ+0.1 mg/ml pentamer (NAG-glucuronic acid)5+1 nM retinol;

400 µM GLZ+0.5 mg/ml pentamer (NAG-glucuronic acid)5+10 nM retinol;

800 µM GLZ+2 mg/ml pentamer (NAG-glucuronic acid) 5+100 nM retinol.

These three solutions have a constant DMSO concentration of 0.2%.

Experimental Protocol:

(Pienimaki et al., *The Journal of Biological Chemistry*, (2001) Vol. 276, No. 23, June 8, p 20428-20435).

The reaction system is constituted of normal human keratinocytes as a monolayer culture in 24-well plates (cells at confluence at the beginning of the incubation).

The NHK are incubated in the presence of the test products and of radiolabeled glucosamine for 6-12-24 and 48 hours, in a final volume of 400 µl of medium per culture well. The incubation temperature is 37° C., the humid atmosphere contains 5% $CO_2$.

a. Recovery of all the GAGs Comprising Radiolabeled Glucosamine:

At the end of the incubation, the culture media are recovered by centrifugation and then the cell layers are rinsed with PBS. The mixture composed of the rinsing medium and of the initial supernatant is recovered. After the addition of hyaluronic acid (10 µg/fraction, role of "carrier" during the precipitations with cetyl pyridinium chloride (CPC)) and of papain (200 µg/fraction, hydrolysis of proteoglycans with release of GAGs), the fractions are incubated for 2 hours at 60° C., and then the fractions are incubated for 10 minutes at 100° C. in order to inactivate the enzymes by heat denaturation. Finally, the GAGs are precipitated by the addition of CPC (final concentration of 1%) and incubated overnight at ambient temperature. After centrifugation for 10 minutes at 15 000 g, and then elimination of the supernatants containing the non-incorporated radiolabeled glucosamine, the pellets are rinsed with 1% CPC, and a further centrifugation of 10 minutes at 15 000 g is carried out, followed by elimination of the supernatants.

b. Measurement of Hyaluronic Acid Neosynthesis:

The hyaluronic acid contained in the centrifugation pellets is specifically hydrolyzed by incubation (3 hours at 37° C.) of these pellets with hyaluronidase (hyaluronan lyase from *Streptomyces hyalurolyticus*, 0.25 unit/fraction). For this, the medium containing these pellets and the hyaluronidase are incubated for 3 hours at ambient temperature, followed by centrifugation for 10 minutes at 15 000 g. Finally, the non-hydrolyzed GAGs are precipitated by adding CPC (1% final concentration) in the presence of chondroitin sulfate (50 µg/fraction—role of "carrier"). The radioactivity of the supernatant, determined by liquid scintillation (β-counter), is directly proportional to the amount of hyaluronic acid neosynthesized during the incubation of the cells with the radiolabeled glucosamine.

The radioactivity measurements are given in the following tables:

TABLE 1

Measurement of hyaluronic acid neosynthesis by normal human keratinocytes in the absence of the "GLZ + pentamer (NAG-glucuronic acid)5 + retinol" combination (control).

|  | Incubation 6 h | Incubation 12 h | Incubation 24 h | Incubation 48 h | Incubation 72 h |
|---|---|---|---|---|---|
| dpm | 4156 | 12 216 | 38 404 | 62 938 | 64 701 |
|  | 3997 | 11 874 | 34 050 | 70 271 | 74 910 |
|  | 4232 | 12 463 | 30 264 | 62 411 | 79 646 |
| Mean | 4128 | 12 184 | 34 239 | 65 207 | 73 086 |
| Standard deviation | 120 | 296 | 4073 | 4394 | 7638 |

TABLE 2

Measurement of hyaluronic acid neosynthesis by normal human keratinocytes in the presence of the "GLZ + pentamer (NAG-glucuronic acid)5 + retinol" combination.

|  | Incubation 6 h | Incubation 12 h | Incubation 24 h | Incubation 48 h | Incubation 72 h |
|---|---|---|---|---|---|
| 100 µM GLZ + 0.1 mg/ml pentamer (NAG-glucuronic acid)5 + 1 nM retinol | | | | | |
| dpm | 3508 | 12 844 | 28 289 | 51 974 | 63 822 |
|  | 3388 | 14 053 | 26 971 | 55 088 | 64 251 |
|  | 3697 | 13 347 | 30 200 | 56 652 | 61 504 |
| Mean | 3531 | 13 415 | 28 487** | 54 571** | 63 192** |
| Standard deviation | 156 | 607 | 1624 | 2381 | 1478 |
| 400 µM GLZ + 0.5 mg/ml pentamer (NAG-glucuronic acid)5 + 10 nM retinol | | | | | |
| dpm | 3672 | 9847 | 25 363 | 26 813 | 54 202 |
|  | 3698 | 10 724 | 27 404 | 36 235 | 49 799 |
|  | 3461 | 10 577 | 25 351 | 29 007 | 54 488 |
| Mean | 3610 | 10 383*** | 26 039*** | 30 685*** | 52 830*** |
| Standard deviation | 130 | 470 | 1182 | 4930 | 2629 |
| 800 µM GLZ + 2 mg/ml pentamer (NAG-glucuronic acid)5 + 100 nM retinol | | | | | |
| dpm | 3203 | 8263 | 17 640 | 32 714 | 33 910 |
|  | 3401 | 8875 | 19 682 | 30 070 | 29 693 |
|  | 2580 | 7590 | 21 320 | 29 092 | 29 194 |
| Mean | 3061 | 8243*** | 19 547*** | 30 625*** | 30 932*** |
| Standard deviation | 428 | 643 | 1844 | 1874 | 2591 |

**mean significantly different than that of the control group (p < 0.05)
***mean significantly different than that of the control group (p < 0.01)

Figure 2:
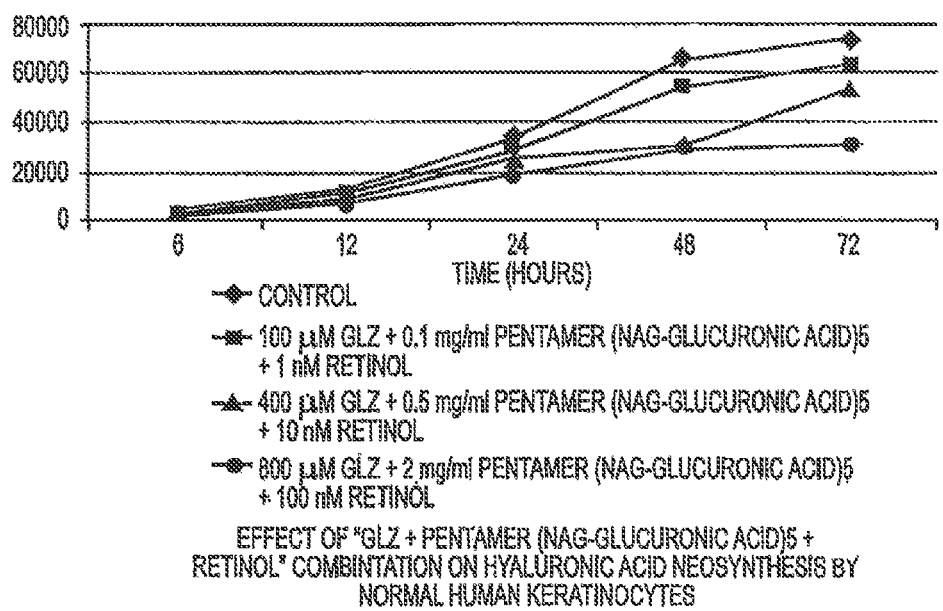
FIG. 2 shows the results of a study, the objective of which was to evaluate the effect of the combination "GLZ+pentamer (NAG-glucuronic acid)5+retinol" on the neosynthesis of hyaluronic acid by normal human keratinocytes.

The inhibitory effect of the "GLZ+pentamer (NAG-glucuronic acid)5+retinol" combination on the hyaluronic acid neosynthesis by normal human keratinocytes is shown in FIG. 2.

The results obtained show a marked inhibition of hyaluronic acid neosynthesis. This effect is dose-dependent and, at the highest concentrations of the three components, the inhibition of neosynthesis is of the order of 50% to 60%. Owing to the pre-existing equilibrium from neosynthesis and degradation of hyaluronic acid, this observed inhibition of neosynthesis corresponds to an equivalent inhibition of degradation.

One may therefore conclude that the effect of the combination protects hyaluronic acid against degradation. This system therefore makes it possible to increase the biostability of hyaluronic acid and, consequently, to improve its bioavailability.

Example 3

Composition No. 1

Injectable Solution No. 1 Containing the 4 Components:

This composition is prepared in a manner that is conventional for those skilled in the art;

| Hyaluronic acid | 2% |
|---|---|
| Glycyrrhizin | 0.02% |
| Pentamer (NAG-glucuronic acid)5 | 0.002% |
| Retinol | 0.00001% |
| Water | qs 100% |

Example 4

Composition No. 2

Injectable Solution No. 2 Containing Hyaluronic Acid, Coupled with a Cream Containing the Other 3 Components:

Injectable Solution:

| Hyaluronic acid | 2% |
|---|---|
| Water | qs 100% |

Cream:

| Glycyrrhizin | 0.02% |
|---|---|
| Pentamer (NAG-glucuronic acid)5 | 0.002% |
| Retinol | 0.00001% |
| Stearic acid | 3.00% |
| Mixture of glyceryl monostearate | 2 |

-continued

| | |
|---|---|
| and PEG stearate (100 EO) | 2.5% |
| PEG stearate (20 EO) | 1.0% |
| Cyclopentadimethylsiloxane | 10.00% |
| Plant oils | 7.00% |
| Synthetic oils | 6.00% |
| Silicone gum | 0.20% |
| Stearyl alcohol | 1.00% |
| Water | qs 100% |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A pharmaceutical/cosmetic composition,
wherein the composition comprises a dermatologically effective amount of at least one inhibitor of hyaluronic acid degradation, at least one hyaluronic acid oligomer, and at least one retinoid and/or salt and/or ester thereof, formulated into a physiologically acceptable medium,
wherein the inhibitor of hyaluronic acid degradation is selected from the group consisting of glycyrrhizin, glycyrrhetinic acid, a salt of glycyrrhizin, and a salt of glycyrrhetinic acid,
wherein the hyaluronic acid oligomer is selected from the group consisting of hyaluronic acid tetramer, hyaluronic acid pentamer, and hyaluronic acid hexamer, and
wherein a concentration of the at least one inhibitor of hyaluronic acid degradation is 100 µM to 800 µM, a concentration of the at least one hyaluronic acid oligomer is 0.1 mg/ml to 2 mg/ml, and a concentration of the at least one retinoid and/or salt and/or ester thereof is 1 nM to 100 nM.

2. The composition according to claim 1, wherein the hyaluronic acid pentamer is the pentamer (NAG-glucuronic acid)5.

3. The composition according to claim 1, wherein the at least one retinoid comprises retinol.

4. The composition according to claim 1, wherein the composition comprises glycyrrhizin, pentamer (NAG-glucuronic acid)5, and retinol.

5. The composition according to claim 1, wherein the composition is formulated for topical administration.

6. A method of inhibiting degradation of hyaluronic acid in skin, wherein the method comprises contacting skin cells with the composition of claim 1.

7. A method of inhibiting neosynthesis of hyaluronic acid in skin, wherein the method comprises contacting skin cells with the composition of claim 1.

8. A method for the treatment of wrinkles, fine lines, fibroblast depletions, or scars, wherein the method comprises parenterally administering a composition comprising hyaluronic acid, and topically applying the composition of claim 1 to an individual in need of such treatment.

9. A method for conducting repair surgery on an individual in need of such treatment, wherein the method comprises, before or during such surgery, parenterally administering a composition comprising hyaluronic acid, and topically applying the composition of claim 1 to an individual in need of such treatment.

10. A combination product, wherein the combination product comprises a first composition comprising hyaluronic acid and a second composition comprising the composition of claim 1.

11. The combination product according to claim 10, wherein the first composition is formulated for parenteral administration and the second composition is formulated for topical administration.

12. The combination product according to claim 11, wherein the first composition is formulated as a solution or suspension.

13. The composition of claim 1, wherein the composition consists essentially of a dermatologically effective amount of at least one inhibitor of hyaluronic acid degradation, at least one hyaluronic acid oligomer, and at least one retinoid and/or salt and/or ester thereof, formulated into a physiologically acceptable medium.

14. The composition of claim 1, wherein the composition consists of a dermatologically effective amount of at least one inhibitor of hyaluronic acid degradation, at least one hyaluronic acid oligomer, and at least one retinoid and/or salt and/or ester thereof, formulated into a physiologically acceptable medium.

15. A method of inhibiting degradation of hyaluronic acid, wherein the method comprises administering the composition of claim 1 parenterally and/or topically to an individual in need thereof.

16. The method of claim 6, wherein the skin is on a human patient.

17. The method of claim 7, wherein the skin is on a human patient.

18. The method of claim 6, wherein the method comprises administering the composition by parenteral administration to the skin cells.

19. The method of claim 7, wherein the method comprises administering the composition by parenteral administration to the skin cells.

20. The composition of claim 1, wherein the concentration of the at least one inhibitor of hyaluronic acid degradation is 800 µM, the concentration of the at least one hyaluronic acid oligomer is 2 mg/ml, and the concentration of the at least one retinoid and/or salt and/or ester thereof is 100 nM.

* * * * *